United States Patent
Zhang et al.

(10) Patent No.: US 11,155,571 B2
(45) Date of Patent: Oct. 26, 2021

(54) SALT OF PYRANOSE-SUBSTITUTED HETEROCYCLIC COMPOUND, PREPARATION METHOD THEREFOR AND USE THEREOF

(71) Applicants: Yabao Pharmaceutical Group Co., Ltd., Shanxi (CN); Suzhou Yabao Pharmaceutical R&D Co., Ltd., Jiangsu (CN)

(72) Inventors: Fei Zhang, Jiangsu (CN); Peng Wang, Jiangsu (CN); Lin Zhu, Jiangsu (CN); Lili Sun, Jiangsu (CN)

(73) Assignees: Yabao Pharmaceutical Group Co., Ltd., Shanxi (CN); Suzhou Yabao Pharmaceutical R&D Co., Ltd., Jiangsu (CN)

( * ) Notice: Subject to any disclaimer, the term of this patent is extended or adjusted under 35 U.S.C. 154(b) by 0 days.

(21) Appl. No.: 16/959,810

(22) PCT Filed: Feb. 3, 2019

(86) PCT No.: PCT/CN2019/074667
§ 371 (c)(1),
(2) Date: Jul. 2, 2020

(87) PCT Pub. No.: WO2019/154388
PCT Pub. Date: Aug. 15, 2019

(65) Prior Publication Data
US 2020/0369708 A1  Nov. 26, 2020

(30) Foreign Application Priority Data
Feb. 8, 2018 (CN) .......................... 201810130672.2

(51) Int. Cl.
*C07H 19/23* (2006.01)
*C07H 1/00* (2006.01)

(52) U.S. Cl.
CPC ............... *C07H 19/23* (2013.01); *C07H 1/00* (2013.01); *C07B 2200/13* (2013.01)

(58) Field of Classification Search
None
See application file for complete search history.

(56) References Cited

U.S. PATENT DOCUMENTS

2015/0126469 A1* 5/2015 Fields ...................... A61P 5/50
514/43
2017/0305914 A1* 10/2017 Rabe ................... C07D 487/04

FOREIGN PATENT DOCUMENTS

| CN | 105593229 A | 5/2016 |
| CN | 105636972 A | 6/2016 |
| JP | 2013177462 A | 9/2013 |

OTHER PUBLICATIONS

Gould, International Journal of Pharmaceutics, 33 (1986) 201-217. (Year: 1986).*

* cited by examiner

*Primary Examiner* — Layla D Berry
(74) *Attorney, Agent, or Firm* — Umberg Zipser LLP; Jason Tejani

(57) ABSTRACT

The present application relates to a salt of a pyranose-substituted heterocyclic compound, a preparation method therefor, and use thereof, and in particular, to an acid addition salt of a compound of formula (I) or a prodrug thereof, and further relates to D-glucuronate of a crystalline compound of formula (I) or a prodrug thereof. D-glucuronate of a crystalline compound of formula (II) has particular advantages in terms of crystallizability, subsequent purification, stability, formulation medicinal properties or quality control, and is most applicable for improving the formulation pharmaceutical properties, purity and quality control, as well as large-scale process development of such drugs.

19 Claims, 3 Drawing Sheets

SALT OF PYRANOSE-SUBSTITUTED HETEROCYCLIC COMPOUND, PREPARATION METHOD THEREFOR AND USE THEREOF

The present application claims the priority of the Chinese Patent Application No. 201810130672.2, with the title of "SALT OF PYRANOSE-SUBSTITUTED HETEROCYCLIC COMPOUND, PREPARATION METHOD THEREFOR AND USE THEREOF", filed on Feb. 8, 2018 before the China National Intellectual Property Administration, which is incorporated herein by reference in its entirety.

TECHNICAL FIELD

The present application belongs to the field of medicinal chemistry, and relates to a salt of pyranose-substituted heterocyclic compound, a preparation method therefor and use thereof.

BACKGROUND OF THE INVENTION

The kidney plays a very important role in the body's carbohydrate metabolism. Glucose is filtered in the glomeruli and reabsorbed in the renal proximal tubule. Glucose cannot freely pass through the lipid bilayer of the cell membrane in the organism, and must rely on the glucose transporter on the cell membrane for transportation. Sodium-dependent glucose transporters (SGLTs) are a category of transporter genes family found in the small intestinal mucosa and renal proximal tubule. The process of reabsorption of glucose in kidney is mainly mediated by SGLTs. Among them, SGLT-1 and SGLT-2 are two subtypes of the most concerned. SGLT-1 is mainly distributed in the small intestinal brush border and the distal S3 segment of the renal proximal tubule, and is expressed in a small amount in the heart and trachea. SGLT-1 is a high-affinity transporter with low transport capacity. SGLT-2 is mainly distributed in the S1 segment of the renal proximal tubule, and is a low-affinity transporter with high transport capacity. The main physiological function of SGLT-2 is to achieve the reabsorption of 90% glucose in glomerular filtration fluid in the renal proximal tubule, and the reabsorption of remaining 10% glucose is achieved by SGLT-1.

Kissei pharmaceutical Co., Ltd. reported that compounds with the following general structure have inhibitory activity against SLGT-1 and/or SGLT-2, and can inhibit the rise of blood glucose level or normalize the blood glucose level:

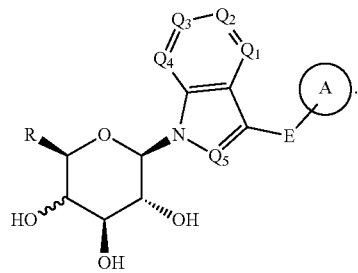

Subsequently, Eli Lilly and Company also reported the following glucopyranosyl-substituted indole-urea derivatives and their use as SGLT-1 inhibitors:

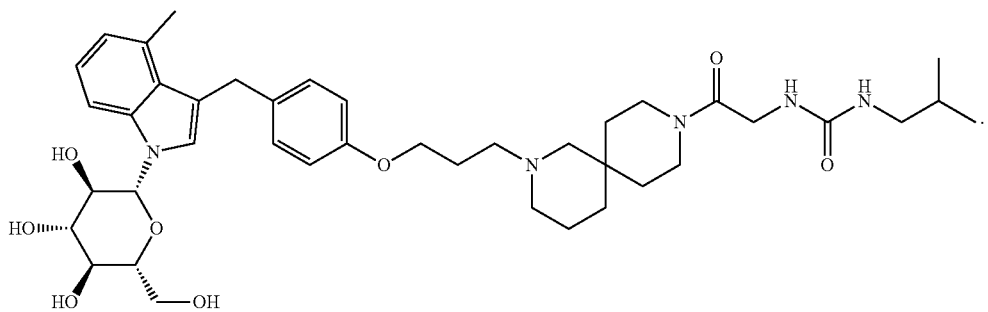

So far, no literature has reported on the crystal forms of the above-mentioned indole-urea derivatives or their salt forms. Those skilled in the art know that the discovery of pharmaceutical compounds and their forms which are more conducive to the purification and quality control has great significance for improving the production and quality control of the pharmaceuticals, and the development prospects of solid oral formulations. Although polymorphism of pharmaceutical compounds is relatively common, for a particular pharmaceutical, it is often necessary to carry out a large amount of synthesis and screening procedures to determine which one/ones of compound per se or its various salt forms is/are more suitable for purification and quality control, and more suitable for the preparation of drugs, and it is also necessary to adjust constantly the compound and its salt forms, or even their combination with solvents, in order to obtain the desired products. In addition, the development of products with improved efficacy on this basis has become a further long-term demand. Therefore, one of the important tasks of pharmaceutical workers includes discovering those compounds or their salt forms that are closely related to the purification, quality control, and the form of drugs prepared, and committing to early elimination of those compounds with poor prospects for purification, quality control and the preparation of drugs. However, the solutions to these problems are rarely as simple as they look like afterwards. An efficient development process of medicament must focus on a comprehensive consideration of product quality, repeatability, durability and cost-effectiveness.

Therefore, since the properties of the above-mentioned indole-urea derivatives, such as crystallizability, purity, druggability, quality control, etc., still need to be improved, it is necessary to develop suitable forms of the above-mentioned indole-urea derivatives and preparation method thereof.

SUMMARY OF THE INVENTION

To solve the above technical problems, the present application provides an acid addition salt of a compound represented by formula (I) or a prodrug thereof:

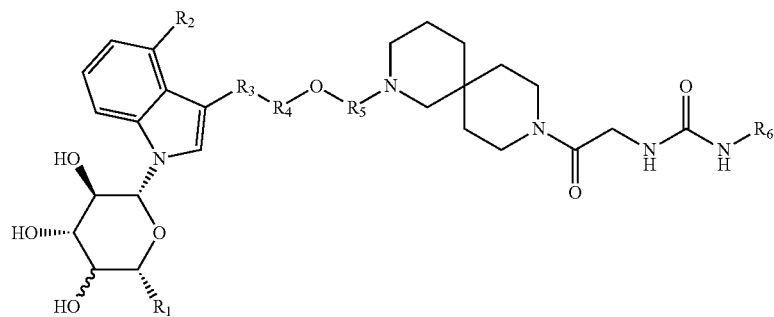

(I)

wherein $R_1$, $R_2$ and $R_6$ are the same or different from each other, and independently selected from $C_1$-$C_8$ alkyl which is unsubstituted or optionally substituted with one or more $R_a$;

$R_3$ and $R_5$ are the same or different from each other, and independently selected from —$(CH_2)_n$— which is unsubstituted or optionally substituted with one or more $R_b$;

$R_4$ is selected from $C_6$-$C_{20}$ aryl which is unsubstituted or optionally substituted with one or more $R_c$;

$R_a$, $R_b$, $R_c$ are the same or different from each other, and independently selected from the group consisting of halogen, hydroxyl, mercapto, nitro and amino;

n is an integer of 1 to 10; and the acid addition salt is selected from the group consisting of maleate, hydrochloride, sulfate, phosphate, citrate, fumarate, gentisate, tartrate and D-glucuronate.

The acid addition salt comprises an acid addition salt of the compound represented by formula (I) or an acid addition salt of the prodrug of the compound represented by formula (I);

the prodrug is an ester formed by a hydroxyl group of the compound represented by formula (I) with a first acid; the hydroxyl group is preferably a hydroxyl group on saccharide moiety; the first acid is preferably a carboxylic acid, a phosphoric acid, or a sulfonic acid; more specifically, the carboxylic acid can be selected from the group consisting of formic acid, acetic acid, benzoic acid and phenylacetic acid; the sulfonic acid can be selected from methanesulfonic acid or benzenesulfonic acid.

Some embodiments of the present application relate to the aforementioned acid addition salts, wherein the groups in the compound represented by formula (I) can be independently selected from the groups as defined below:

$R_1$ can be selected from the group consisting of —$CH_3$, —$CH_2CH_3$, —$CH_2Cl$, —$CH_2F$, —$CH_2OH$ and —$CH_2SH$;

$R_2$ can be selected from the group consisting of —$CH_3$, —$CH_2CH_3$ and —$CH_2CH_2CH_3$;

$R_3$ can be selected from the group consisting of —$CH_2$—, —$(CH_2)_2$— and —$(CH_2)_3$—;

$R_4$ can be Ph-;

$R_5$ can be selected from the group consisting of —$CH_2$—, —$(CH_2)_2$— and —$(CH_2)_3$—; and $R_6$ can be selected from the group consisting of —$CH_3$, —$CH_2CH_3$, —$CH_2CH_2CH_3$, —$CH(CH_3)_2$, —$CH(CH_3)CH_2CH_3$ and —$CH_2CH(CH_3)_2$.

The acid addition salt can be selected from the group consisting of sulfate, phosphate, tartrate and D-glucuronate.

Preferably, in the acid addition salt, a molar ratio of the compound represented by formula (I) to a second acid that forms the acid addition salt is 1:1.

Preferably, the formula (I) has a structure represented by formula (II):

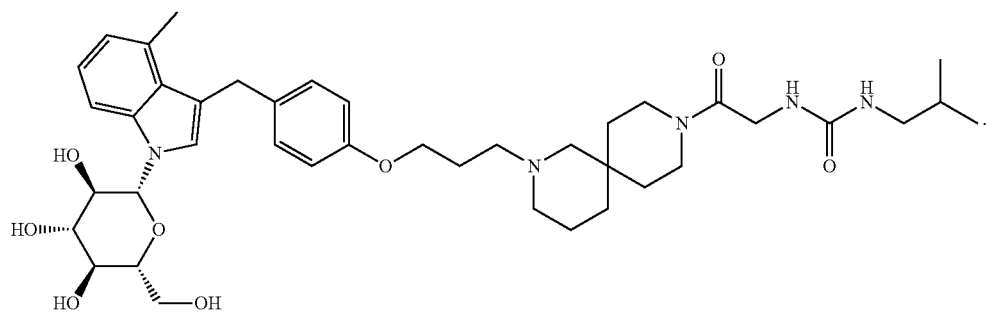

(II)

The present application also provides a method for preparing the aforementioned acid addition salt, comprising reacting the compound represented by formula (I) or the prodrug thereof with a second acid.

The second acid is an acid required for preparing the acid addition salt. In some embodiments of the present application, the second acid can be selected from the group consisting of sulfuric acid, phosphoric acid, tartaric acid, and D-glucuronic acid.

Preferably, the reaction is carried out in the presence of a solvent. The solvent is not particularly limited, preferably those capable of dissolving the compound represented by formula (I).

As an example, the solvent can be one, two, or more selected from the group consisting of alcohols solvent, ketones solvent, ethers solvent, esters solvent, and the like.

For example, the alcohols solvent can be selected from the group consisting of methanol, ethanol, isopropanol, butanol, pentanol, decanol, n-dodecyl alcohol, cyclopentanol, cyclohexanol, benzyl alcohol, and phenylethanol;

the ketones solvent can be selected from the group consisting of acetone, 2-butanone, methyl isopropyl ketone, methyl cyclohexanone, cyclohexanone, and methyl isobutyl ketone;

the ethers solvent can be selected from the group consisting of diethyl ether, methyl ethyl ether, methyl tert-butyl ether, dipropyl ether, dibutyl ether, 1,4-dioxane, and tetrahydrofuran; and the esters solvent can be selected from the group consisting of ethyl acetate, hexyl acetate, methyl acetate, and isopropyl acetate.

In some embodiments of the aforementioned method for preparing the acid addition salt, the reaction can be performed at a temperature in the range of 0-30° C., for example, 15-30° C., such as 20-25° C.

In some embodiments of the aforementioned method for preparing the acid addition salt, a molar ratio of the compound represented by formula (I) or the prodrug thereof to the second acid can be greater than or equal to 1:1, preferably 1:(1-2), for example, 1:(1-1.5), such as 1:(1-1.2).

The present application also provides a crystal form of the acid addition salt of the compound represented by formula (I) or the prodrug thereof, for example, a crystal form of D-glucuronate of the compound represented by formula (I) or the prodrug thereof. As an example, the present application provides a crystal form of the acid addition salt of the compound represented by formula (II) or the prodrug thereof, for example, a crystal form of D-glucuronate of the compound represented by formula (II) or the prodrug thereof.

As an example, the crystal form is one or more selected from the group consisting of the crystal forms described below.

The present application provides a crystal form A of D-glucuronate of the compound represented by formula (II), having one or more characteristic peaks at 4.3±0.2°, 9.2±0.2°, 12.7±0.2°, 13.9±0.2°, 16.9±0.2° and 21.9±0.2° represented by 2θ angle in an X-ray powder diffraction (XRPD) pattern, wherein the compound represented by formula (II) is as defined above.

Preferably, the crystal form A has an X-ray powder diffraction pattern substantially same as shown in FIG. 1.

Preferably, the thermogravimetric analysis (TGA) spectrum of the crystal form A shows a weight loss at about 140° C., for example, a weight loss more than 15%, such as a weight loss of 15.3%.

Preferably, the crystal form A has a thermogravimetric analysis spectrum substantially same as shown in (a) of FIG. 2.

Preferably, the differential scanning calorimetry (DSC) spectrum of the crystal form A shows endothermic peaks at about 107.4° C. and 130.5° C.

Preferably, the crystal form A has a differential scanning calorimetry spectrum substantially same as shown in (b) of FIG. 2.

The present application also provides a method for preparing the crystal form A, comprising reacting the compound represented by formula (II) with D-glucuronic acid in a mixed solvent of tetrahydrofuran and water, and drying after completion of the reaction to obtain the crystal form A.

According to the method for preparing the crystal form A of the present application, the method comprises stirring the compound of formula (II) and D-glucuronic acid in the mixed solvent of tetrahydrofuran and water, separating a solid, and drying to obtain the crystal form A.

Preferably, the separating is centrifugal separation.

Preferably, the stirring is performed at a speed of 1000 rpm (rev/min) for more than 7 days.

Preferably, the drying is vacuum drying for more than 2 hours.

In some embodiments of the method for preparing the crystal form A of the present application, a molar ratio of the compound represented by formula (II) to D-glucuronic acid can be 1:(1-1.1), for example, 1:(1-1.05), such as 1:(1-1.03).

In some embodiments of the method for preparing the crystal form A of the present application, a ratio of the mass (g) of the compound represented by formula (II) to the volume (mL) of the mixed solvent can be 1.25:(5-20), such as 1.25:(5-15), such as 1.25:10.

In some embodiments of the method for preparing the crystal form A of the present application, a volume ratio of tetrahydrofuran to water can be 19:(0.5-1.5), preferably 19:1.

The present application also provides crystal form D of D-glucuronate of the compound represented by formula (II), having one or more characteristic peaks at 8.5±0.2°, 11.8±0.2°, 18.6±0.2°, and 21.5±0.2° represented by 2θ angle in the X-ray powder diffraction pattern.

Preferably, the crystal form D has an X-ray powder diffraction pattern substantially same as shown in FIG. 3.

Preferably, the thermogravimetric analysis spectrum of the crystal form D shows a weight loss at about 140° C., for example, a weight loss more than 9%, such as a weight loss of 9.3%.

Preferably, the crystal form D has a thermogravimetric analysis spectrum substantially same as shown in (a) of FIG. 4.

Preferably, the differential scanning calorimetry spectrum of the crystal form D shows an endothermic peak at about 82.5° C.

Preferably, the crystal form D has a differential scanning calorimetry spectrum substantially same as shown in (b) of FIG. 4.

According to the present application, the solubility of the crystal form D in water is greater than 30 mg/mL, which is significantly improved compared to that of the compound represented by formula (II) (solubility <2.3 mg/mL).

The present application also provides a method for preparing the aforementioned crystal form D, comprising stirring the crystal form A of D-glucuronate of the compound represented by formula (II) in 2-butanone, 1,4-dioxane or a mixture thereof, separating a solid, and drying to obtain the crystal form D.

Preferably, the method for preparing the crystal form D comprises suspending and stirring the crystal form A of D-glucuronate of the compound represented by formula (II) in 2-butanone, 1,4-dioxane or the mixture thereof overnight.

Preferably, the separating is centrifugal separation.

In some embodiments of the method for preparing the crystal form D of the present application, a ratio of the mass (g) of the crystal form A to a total volume (mL) of 2-butanone, 1,4-dioxane, or a mixture thereof can be 2:(5-15), for example, 2:(5-10), for example, 2:10.

The present application also provides a crystal form C of D-glucuronate of the compound represented by formula (II), having an X-ray powder diffraction pattern substantially same as shown in a pattern of a crystal form C in FIG. 5.

The present application also provides a method for preparing the crystal form C, comprising suspending and stirring the crystal form A of D-glucuronate of the compound represented by the formula (II) in isopropanol, separating a solid, and drying to obtain the crystal form C.

Preferably, the drying is vacuum drying for more than 2 hours, and the separating is centrifugal separation.

In some embodiments of the method for preparing the crystal form C of the present application, a ratio of the mass (g) of the crystal form A to the volume (mL) of isopropanol can be 2:(5-15), for example, 2:(5-10), for example, 2:10.

The present application also provides a crystal form E of D-glucuronate of the compound represented by formula (II), having an X-ray powder diffraction pattern substantially same as shown in a pattern of a crystal form E in FIG. 5.

The present application also provides a method for preparing the crystal form E, comprising suspending and stirring the crystal form A of D-glucuronate of the compound represented by the formula (II) in toluene, separating a solid, and drying to obtain the crystal form E.

Preferably, the drying is vacuum drying for more than 2 hours, and the separating is centrifugal separation.

In some embodiments of the method for preparing the crystal form E of the present application, a ratio of the mass (g) of crystal form A to the volume (mL) of toluene can be 2:(5-15), for example, 2:(5-10), for example, 2:10.

The present application also provides a crystal form F of D-glucuronate of the compound represented by formula (II), having an X-ray powder diffraction pattern substantially same as shown in a pattern of a crystal form F in FIG. 5.

The present application also provides a method for preparing the crystal form F, comprising suspending and stirring the crystal form A of D-glucuronate of the compound represented by the formula (II) in dichloromethane, separating a solid, and drying to obtain the crystal form F.

Preferably, the drying is vacuum drying for more than 2 hours, and the separating is centrifugal separation.

In some embodiments of the method for preparing the crystal form F of the present application, a ratio of the mass (g) of the crystal form A to the volume (mL) of dichloromethane can be 2:(5-15), for example, 2:(5-10), for example, 2:10.

The present application also provides a pharmaceutical composition comprising the aforementioned acid addition salt of the compound represented by formula (I) or the prodrug thereof, or the aforementioned crystal form of the acid addition salt, and a pharmaceutically acceptable excipient.

The present application also provides a pharmaceutical composition comprising the aforementioned crystal form of D-glucuronate of the compound represented by formula (I) or the prodrug thereof, and a pharmaceutically acceptable excipient.

The present application also provides a pharmaceutical composition comprising the D-glucuronate of the compound represented by formula (II) and a pharmaceutically acceptable excipient.

Preferably, the D-glucuronate of the compound represented by formula (II) comprises 50% by weight or more of the crystal form of D-glucuronate of the compound represented by formula (II).

The present application further provides a pharmaceutical composition comprising one, two, or any combination of the crystal forms A, C, D, E, and F of D-glucuronate of the compound represented by formula (II), and a pharmaceutical acceptable excipient.

In some embodiments of the pharmaceutical composition of the present application, the pharmaceutical composition can be a formulation. Specifically, the formulation can be administered orally, parenterally, transmucosally, nasally, topically, or sublingually, for example, the formulation can be an oral formulation, such as a tablet or a capsule.

In some embodiments of the pharmaceutical composition of the present application, the amount of the active ingredient including the acid addition salt of the compound represented by formula (I) or the prodrug thereof, the aforementioned crystal forms and/or the crystal forms A, C, D, E and/or F of D-glucuronate of the compound represented by formula (II) in the pharmaceutical composition is a therapeutically or prophylactically effective amount, which can be about 0.10 mg to about 150 mg per day, such as about 5 mg to about 50 mg per day.

The present application also provides the use of the acid addition salt of the compound represented by formula (I) or the prodrug thereof, the aforementioned crystal form, and the aforementioned pharmaceutical composition in the manufacture of a medicament.

The present application also provides the use of D-glucuronate of the compound represented by formula (I) or the prodrug thereof, the crystal form thereof and a pharmaceutical composition comprising at least one of them in the manufacture of a medicament.

The present application also provides the use of D-glucuronate of the compound represented by formula (II) and a pharmaceutical composition comprising the same in the manufacture of a medicament.

The present application further provides the use of the crystal form of D-glucuronate of the compound represented by formula (II), such as the crystal form A, C, D, E or F, and a pharmaceutical composition comprising at least one of them in the manufacture of a medicament.

Preferably, the medicament can be used to prevent and/or treat diseases or disorders mediated by SGLT-1 or SGLT-2, such as hyperglycemia-related diseases, impaired glucose tolerance (IGT), impaired fasting glucose (IFG) or metabolic syndrome or the like.

For example, the hyperglycemia-related diseases can be diabetes, such as type I diabetes or type II diabetes.

The present application also provides the use of the aforementioned acid addition salt, the aforementioned crystal form, or the aforementioned pharmaceutical composition for preventing and/or treating diseases or disorders. Preferably, the aforementioned acid addition salt is the crystal form of D-glucuronate of the compound represented by formula (I) or the prodrug thereof, D-glucuronate of the compound represented by formula (II) or the crystal form A, C, D, E or F thereof.

The diseases or disorders can be the above-mentioned diseases or disorders mediated by SGLT-1 or SGLT-2.

The present application also provides a method for preventing and/or treating diseases or disorders, comprising administering a therapeutically effective amount of the aforementioned acid addition salt, the aforementioned crystal form, or the aforementioned pharmaceutical composition to a patient in need thereof; and the diseases or disorders can be the above-mentioned diseases or disorders mediated by SGLT-1 or SGLT-2.

Definition and Explanation of Terms

Unless otherwise defined, all scientific and technical terms herein have the same meaning as commonly understood by those skilled in the art. Unless otherwise stated, all patents, patent applications, and publications cited herein are incorporated herein by reference in their entireties.

The numerical range described in the specification and claims of the present application should be understood as describing the two endpoints of the range and each integer in the range, when the numerical value is understood as an "integer". For example, "integer of 1-10" should be understood as describing each integer of 1, 2, 3, 4, 5, 6, 7, 8, 9, and 10. The numerical range should be understood as describing the two endpoints of the range, each integer in the range and each decimal in the range, when the numerical value is understood as a "number". For example, "the number of 1-10" should be understood as not only describing each integer of 1, 2, 3, 4, 5, 6, 7, 8, 9, and 10, but also describing at least the sum of the each integer and 0.1, 0.2, 0.3, 0.4, 0.5, 0.6, 0.7, 0.8, 0.9, respectively.

The term "$C_1$-$C_8$ alkyl" should be understood as a linear or branched saturated monovalent hydrocarbyl having 1, 2, 3, 4, 5, 6, 7 or 8 carbon atoms. The alkyl is, for example, methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl, or their isomers. In particular, the alkyl has 1, 2, 3, 4, 5 or 6 carbon atoms ("$C_1$-$C_6$ alkyl"), such as methyl, ethyl, propyl, butyl, isopropyl, isobutyl, sec-butyl, tert-butyl, more particularly, the alkyl has 1, 2 or 3 carbon atoms ("$C_1$-$C_3$ alkyl"), such as methyl, ethyl, n-propyl or isopropyl.

The term "$C_6$-$C_{20}$ aryl" should be understood as a monovalent or divalent aromatic monocyclic, bicyclic or tricyclic hydrocarbon ring having 6 to 20 carbon atoms, preferably "$C_6$-$C_{14}$ aryl". The term "$C_6$-$C_{14}$ aryl" should be understood as preferably representing a monovalent or divalent aromatic monocyclic, bicyclic or tricyclic hydrocarbon ring having 6, 7, 8, 9, 10, 11, 12, 13 or 14 carbon atoms, in particular a ring having 6 carbon atoms ("$C_6$ aryl"), such as phenyl; or biphenyl, or a ring having 9 carbon atoms ("$C_9$ aryl"), such as indanyl or indenyl, or a ring having 10 carbon atoms ("$C_{10}$ aryl"), such as tetrahydronaphthyl, dihydronaphthyl, or naphthyl, or a ring having 13 carbon atoms ("$C_{13}$ aryl"), such as fluorenyl, or a ring having 14 carbon atoms ("$C_{14}$ aryl"), such as anthryl.

The term "halogen" refers to fluorine, chlorine, bromine and iodine.

The term "acid addition salt of a compound or a prodrug thereof" refers to an acid addition salt of the compound or an acid addition salt of the prodrug of the compound.

The term "crystal form" refers to the solid state of the compound of the present application. It should be understood that when a substance changes from an amorphous state to a crystalline state, its molecules will gradually change from a relatively disordered arrangement state to a relatively ordered arrangement state. For this reason, the term "crystal form" described in the present application should be understood as a substance having an ordered or relatively ordered solid state, for example, including each polymorph described in the present application.

The crystal form of D-glucuronate of the compound represented by formula (II) or the prodrug thereof described in the present application can be a solvate of D-glucuronate of the compound represented by formula (II) or the prodrug thereof. The solvate may be a solvate formed by D-glucuronate of the compound or the prodrug thereof with one, two or more of alcohols solvent, ketones solvent, ethers solvent, and the like. For example, the alcohols solvent can be selected from the group consisting of methanol, ethanol, isopropanol, butanol, pentanol, decanol, n-dodecyl alcohol, cyclopentanol, cyclohexanol, benzyl alcohol, and phenethyl alcohol; the ketones solvent can be selected from the group consisting of acetone, 2-butanone, methyl isopropyl ketone, methyl cyclohexanone, cyclohexanone, and methyl isobutyl ketone; and the ethers solvent can be selected from the group consisting of diethyl ether, methyl ethyl ether, methyl tert-butyl ether, dipropyl ether, dibutyl ether, 1,4-dioxane, and tetrahydrofuran.

The "pharmaceutically acceptable excipient" used in the pharmaceutical composition described in the present application can be any conventional excipient in the field of pharmaceutical formulation, and the choice of specific excipient will depend on the mode of administration to the specific patient or the type and status of disease. The method for preparing suitable pharmaceutical composition for specific mode of administration is completely within the knowledge of those skilled in the field of pharmaceutical. For example, the pharmaceutically acceptable excipient can include solvents, diluents, dispersants, suspending agents, surfactants, isotonic agents, thickeners, emulsifiers, binders, lubricants, stabilizers, hydrating agents, emulsification accelerators, buffers, absorbents, colorants, ion exchangers, mold release agents, coating agents, corrigents, antioxidants, and the like commonly used in the field of pharmaceutical. If necessary, flavoring agents, preservatives, sweeteners and the like can be also added into the pharmaceutical composition.

The "therapeutically or prophylactically effective amount" described in the present application refers to the amount of the active ingredient such as the aforementioned acid addition salt, the aforementioned crystal form that can at least prevent or reduce the symptoms of the patient's disorder when administered to the patient. The actual amount containing a "therapeutically or prophylactically effective amount" will vary depending on a variety of conditions, including but not limited to the specific disorder to be treated, the severity of the disorder, the patient's physical and health status, and route of administration. Skilled medical practitioners can easily determine the appropriate amount using methods known in the medical field.

Beneficial Effects

The inventors of the present application obtained a large number of acid addition salts of the compound of formula (I) through experiments, and unexpectedly found in the study on numerous acid addition salts that D-glucuronate of the compound of formula (II) has significant advantages, in particular in terms of crystallizability, subsequent purification, stability, druggability or quality control, and is suitable for improving the druggability, purity and quality control of such medicaments, and is suitable for improving the large-scale process development of such medicaments. In the medicaments of the prior art, there is no a unique salt form formed by the compound of formula (II) or a structure similar thereto with D-glucuronic acid having the above-mentioned characteristics superior to other salt form, as discovered in the present application. Without wishing to be bound by theory, the inventors believe that this may be due to the unique microscopic chemical structure of D-glucuronic acid and the compound of formula (II) capable of forming a solid product that is more stable and easier to be precipitated from conventional solvents, thus the acid addition salts of the present application are particularly suitable for overcoming the shortcomings in the prior art and for developing the pharmaceutical druggability and large-scale process to achieve good yield and purity, under the premise of controlling the cost and applying mild reaction conditions.

BRIEF DESCRIPTION OF THE DRAWINGS

In order to describe the examples of the present application and the technical solutions of the prior art more clearly, the drawings required in the examples and the prior art are briefly introduced below. Obviously, the drawings described as below are only some examples of the present application, for those ordinary skilled in the art, other drawings can be also obtained based on these drawings without creative efforts.

DETAILED DESCRIPTION OF THE INVENTION

The technical solutions of the present application will be further described in detail below with reference to exemplary examples. It should be understood that the following examples are only illustrative for describing and explaining the present application, which should not be interpreted as limiting the scope of protection of the present application. The technical solutions implemented based on the above contents of the present application are all covered by the scope of protection of the present application.

Unless otherwise stated, the raw materials and reagents used in the following examples are commercially available, or can be prepared by known methods.

Instruments and Test Methods

XRPD patterns were collected on PANalytacal XPERT-3 and Bruker D2 X-ray powder diffraction analyzers. X-ray: Cu, Kα, Kα1 (Å): 1.540598; Kα2 (Å): 1.544426; intensity ratio of Kα2/K=1:0.50; scan range: 3°-40°.

TGA and DSC spectrums were collected on TA Q500/5000 thermogravimetric analyzer and TAQ200/2000 differential scanning calorimeter, respectively.

Preparation Example 1: Preparation of the Compound Represented by Formula (II)

According to the method described in Example 1b of Chinese invention patent application CN201480054233.8, the compound represented by formula (II) was prepared, and the X-ray powder diffraction pattern showed that it was an amorphous product, and the purity was 97.12%. Unless otherwise stated, the amorphous product obtained in this preparation example was used as the raw material of the compound represented by formula (II) in the following examples.

Example 1: Preparation of D-Glucuronate of the Compound Represented by Formula (II)

About 250 mg of the compound of formula (II) and 1.1 equivalent of D-glucuronic acid (molar ratio of 1:1.1) were weighed and added into 10 mL of acetone, and stirred at about 50-60° C. After the reaction was completed, the mixture was filtered and dried to obtain the D-glucuronate of the compound represented by formula (II). Its mass spectrum data: MS (m/z): 750.5 (M+H); MS (m/z): 193.1 (glucuronic acid-H). After analysis, it was confirmed that the compound obtained is D-glucuronate of the compound of formula (II).

Example 2: Preparation of Crystal form A of D-Glucuronate of the Compound Represented by Formula (II)

Figure 1:
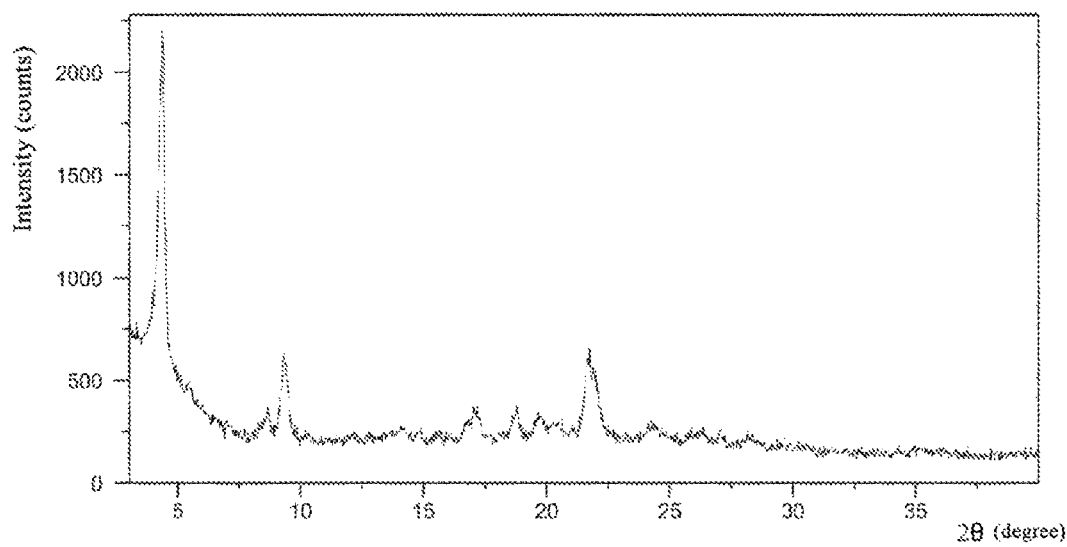
FIG. 1 is an X-ray powder diffraction pattern of the crystal form A of D-glucuronate of the compound represented by formula (II)
Figure 2:
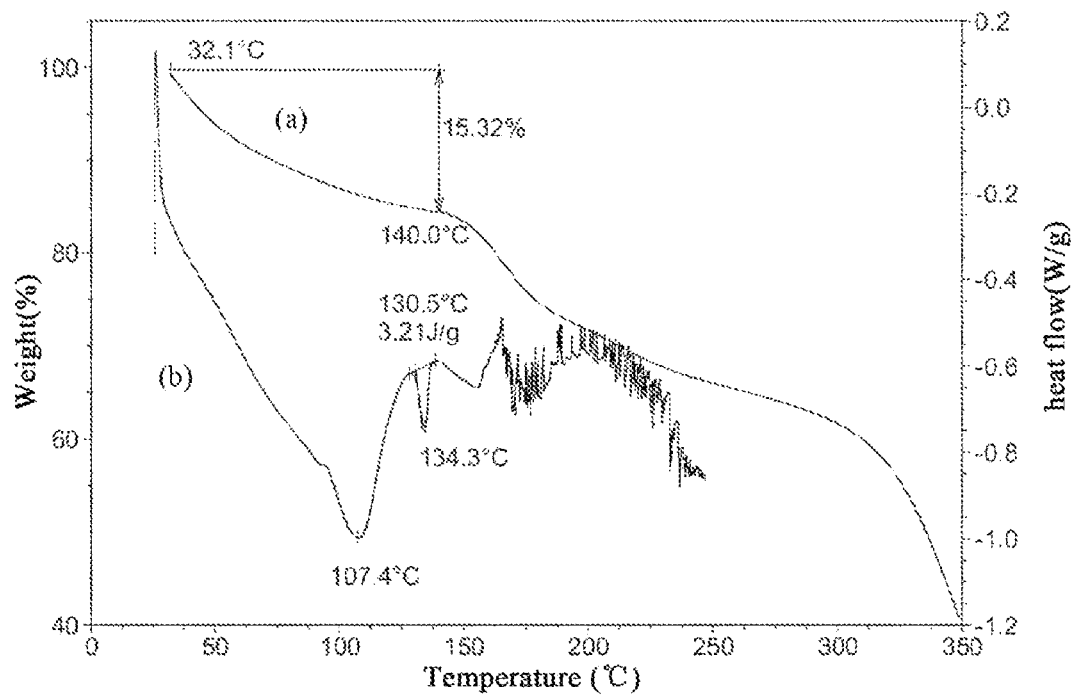
FIG. 2 is a thermogravimetric analysis and differential scanning calorimetry spectrum of the crystal form A of D-glucuronate of the compound represented by formula (II)

The compound represented by formula (II) (3 g), D-glucuronic acid (0.78 g), and 30 mL tetrahydrofuran (containing 5% water by mass) were sequentially added into a 50 mL single-necked bottle, stirred at room temperature for 24 h, and filtered to obtain a solid. The solid was rinsed with 10 mL of tetrahydrofuran, dried under vacuum at 35-40° C. for 2-3 h, and weighed to obtain 4 g of product (moisture 0.15%, THF 5.81%). The X-ray powder diffraction pattern thereof is shown in FIG. 1, and the product is confirmed to be the crystal form A.

Example 3: Preparation of Crystal Form A of D-Glucuronate of the Compound Represented by Formula (II)

The compound represented by formula (II) (250.1 mg) and D-glucuronic acid (66.3 mg) were weighed and added into a 5 mL glass bottle. 2 mL of tetrahydrofuran/water (v:v, 19:1) was added, and the mixture was stirred at 1000 rpm for 7 days. The mixture was centrifuged to obtain a solid. The solid was dried under vacuum at room temperature for 2 h. According to the X-ray powder diffraction pattern, it is confirmed that the crystal form A was obtained.

Example 4: Preparation of Crystal Form C of D-Glucuronate of the Compound Represented by Formula (II)

100 mg of the crystal form A prepared in Example 2 was weighed and added into a 2 mL glass bottle. 0.5 mL of isopropanol was added, and the mixture was suspended and stirred overnight. The mixture was centrifuged to obtain a solid. The solid was dried under vacuum at room temperature for 2 h. According to the X-ray powder diffraction pattern shown in FIG. 5, it is confirmed that the crystal form C was obtained.

Example 5: Preparation of Crystal Form D of D-Glucuronate of the Compound Represented by Formula (II)

Figure 3:
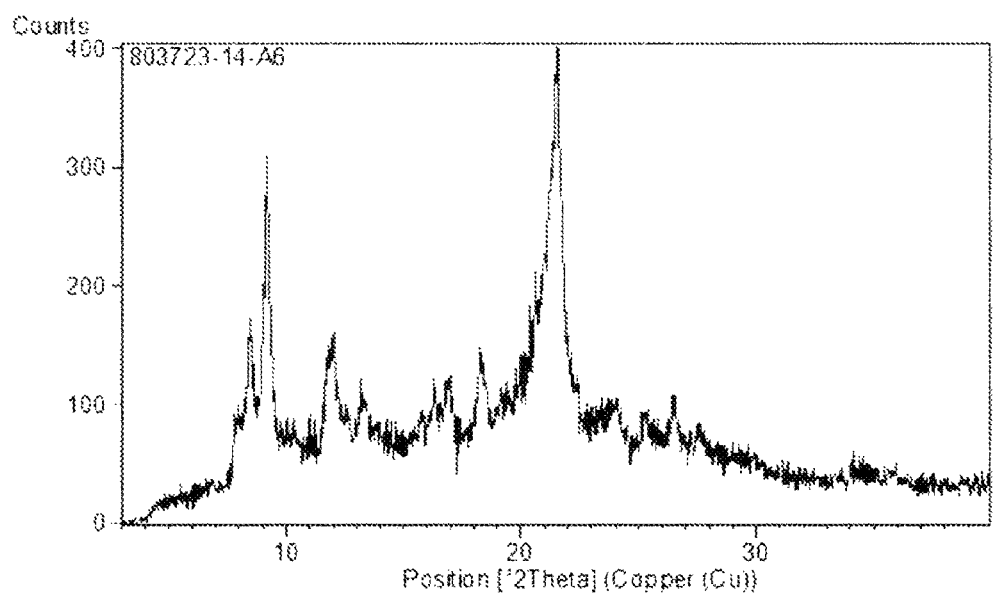
FIG. 3 is an X-ray powder diffraction pattern of the crystal form D of D-glucuronate of the compound represented by formula (II)
Figure 4:
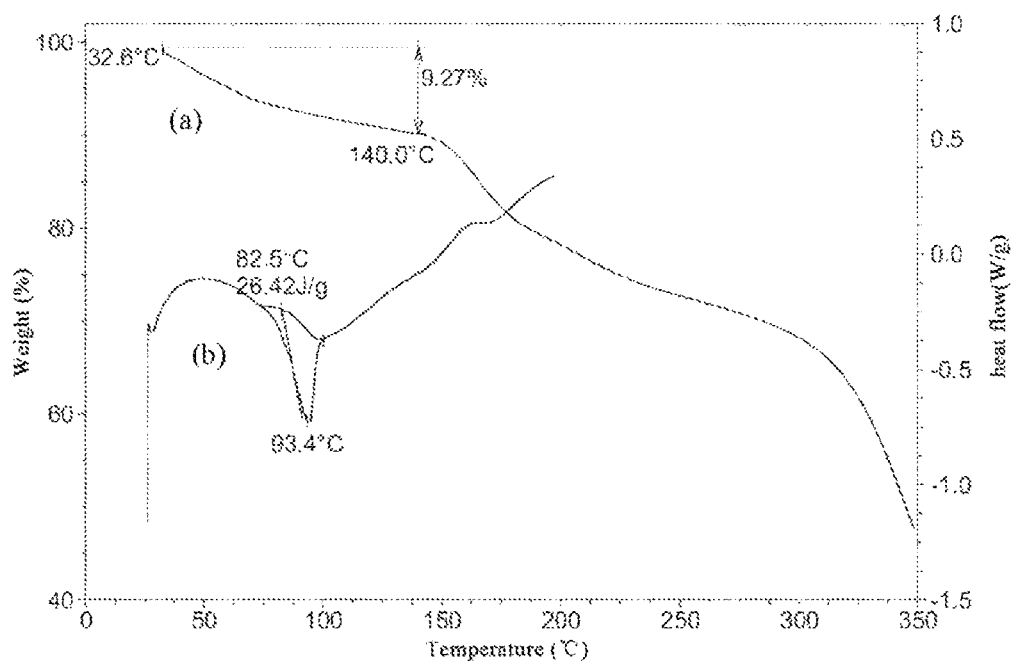
FIG. 4 is a thermogravimetric analysis and differential scanning calorimetry spectrum of the crystal form D of D-glucuronate of the compound represented by formula (II)

1.5 g of the crystal form A was weighed and added into 15 ml of 2-butanone. The mixture was slurried at room temperature for 4-5 h, filtered, and dried under vacuum at 35-40° C. for 2-3 h. According to the X-ray powder diffraction pattern shown in FIG. 3, it is confirmed that the crystal form D was obtained.

Example 6: Preparation of Crystal Form D of D-Glucuronate of the Compound Represented by Formula (II)

100 mg of the crystal form A prepared in Example 2 was weighed and added into a 2 mL glass bottle. 0.5 mL of 2-butanone was added, and the mixture was suspended and stirred overnight. The mixture was centrifuged to obtain a solid. The solid was dried under vacuum at room temperature for 2 h. According to the X-ray powder diffraction pattern, it is confirmed that the crystal form D was obtained.

Example 7: Preparation of Crystal Form D of D-Glucuronate of the Compound Represented by Formula (II)

100 mg of the crystal form A prepared in Example 2 was weighed and added into a 2 mL glass bottle. 0.5 mL of 1,4-dioxane was added, and the mixture was suspended and stirred overnight. The mixture was centrifuged to obtain a solid. The solid was dried under vacuum at room temperature for 2 h. According to the X-ray powder diffraction pattern, it is confirmed that the crystal form D was obtained.

Example 8: Preparation of Crystal Form E of D-Glucuronate of the Compound Represented by Formula (II)

100 mg of the crystal form A prepared in Example 2 was weighed and added into a 2 mL glass bottle. 0.5 mL of toluene was added, and the mixture was suspended and stirred overnight. The mixture was centrifuged to obtain a solid. The solid was dried under vacuum at room temperature for 2 h. According to the X-ray powder diffraction pattern shown in FIG. 5, it is confirmed that the crystal form E was obtained.

Example 9: Preparation of Crystal Form F of D-Glucuronate of the Compound Represented by Formula (II)

100 mg of the crystal form A prepared in Example 2 was weighed and added into a 2 mL glass bottle. 0.5 mL of dichloromethane was added, and the mixture was suspended and stirred overnight. The mixture was centrifuged to obtain a solid. The solid was dried under vacuum at room temperature for 2 h. According to the X-ray powder diffraction pattern shown in FIG. 5, it is confirmed that the crystal form F was obtained.

Example 10: Preparation of Other Salt Forms of the Compound Represented by Formula (II)

Preparation of fumarate of the compound represented by formula (II): 150.5 mg of the compound represented by formula (II) and 23.7 mg of fumaric acid were weighed and added into a 5 ml glass bottle. 3 ml of acetone was added, and the mixture was stirred at 750 rpm for 3 days, and centrifuged to obtain a solid. The solid was dried under vacuum at room temperature for 2 h.

Preparation of gentisate of the compound represented by formula (II): 150.8 mg of the compound represented by formula (II) and 31.7 mg of gentisic acid were weighed and added into a 5 ml glass bottle. 2 ml of ethanol was added, and the mixture was stirred at 750 rpm for 3 days, and centrifuged to obtain a solid. The solid was dried under vacuum at room temperature for 2 h.

The acid addition salts, such as hydrochloride, sulfate, phosphate, acetate, lactate, maleate, succinate, L-malate, adipate, L-tartrate, hippurate, citrate, mucate, ascorbate, benzoate, nicotinate, ethanedisulfonate, oxalate, malonate, p-toluenesulfonate and 2-hydroxyl ethanesulfonate of the compound represented by formula (II) were prepared respectively in a similar manner.

Example 11: Stability Experiment of Crystal Form A of D-Glucuronate and Other Salts of Compound Represented by Formula (II)

After being allowed to stand at 25° C., 60% RH (relative humidity) and unsealed conditions for 7 days, the relative purity and properties of crystal form A obtained in Example 2 did not change, showing good stability, whereas the hydrochloride of the compound represented by formula (II) degraded and the relative purity thereof decreased to 96.8% (the relative purity was calculated as: purity on day 7/purity on day 0*100%).

After being allowed to stand at 80° C. and sealed conditions for 7 days, the relative purity and properties of crystal form A obtained in Example 2 did not change, showing good stability, whereas the hydrochloride of the compound represented by formula (II) degraded and the relative purity thereof decreased to 97.9%; and the maleate and citrate of the compound represented by formula (II) degraded and the relative purity both decreased to 98.5%. In addition, the stability of the crystal forms D, E, and F of D-glucuronate of the compound represented by formula (II) were tested under the same conditions. The results show that these three crystal forms have good stability. The above experiments show that D-glucuronate of the compound represented by formula (II) is more conducive to the preparation of stable crystal forms, and the obtained crystal forms have better stability than other salt forms.

Example 12: Test of Content of Related Substances

Chromatographic Conditions:

| Instrument | Thermo U3000 |
|---|---|
| Column | Welch Xtimate C18 4.6*150 mm, 3.5 μm |
| Column temperature | 45° C. |
| Mobile phase | A: Phosphate buffer solution (1.36 g of potassium dihydrogen phosphate was weighted and added into 1000 ml of water, dissolved with ultrasonic, adjusted the pH to 5.5 with 1 mol/L sodium hydroxide solution) - acetonitrile (80:20) B: Acetonitrile - methanol (90:10) |

| Gradient procedure | Time (min) | A% | B |
|---|---|---|---|
| | 0.0 | 95 | 5 |
| | 2.00 | 95 | 5 |
| | 25.00 | 70 | 30 |
| | 35.00 | 40 | 60 |
| | 40.00 | 40 | 60 |
| | 40.10 | 95 | 5 |
| | 45.00 | 95 | 5 |

| Flow rate | 1.0 ml/min |
|---|---|
| Detector | 225 nm |
| Solvent | Acetonitrile-water (1:1) |
| Sample size | 10 μl |
| Sample concentration | 0.3 mg/ml sample solution, direct sample introduction. |

| | Content of related substances at various retention time (min) of HPIC | | | | | | |
|---|---|---|---|---|---|---|---|
| Sample source | 8.20 | 11.34 | 16.86 | 17.26 | 23.02 | 23.90 | 26.30 |
| Crystal form A (Example 2) | — | — | 99.84 | 0.16 | — | — | — |
| Compound of formula (II) (Preparation Example I) | 0.28 | 0.11 | 97.12 | 0.18 | 1.09 | 0.18 | 0.39 |

16.86 min is the retention time of the compound represented by formula (II).

It can be seen from the results in the above table that the purity of crystal form A prepared from the D-glucuronate of compound represented by formula (II) is significantly improved compared to that of the compound represented by formula (II), indicating that the D-glucuronate of the compound represented by formula (II) has obvious advantages over the compound represented by formula (II) in terms of purity and quality control.

Example 13: Crystallizability Experiment of the Compound Represented by Formula (II)

a. Anti-Solvent Addition Method

About 15 mg of the compound represented by formula (II) was weighed and added into a 5 mL vial, dissolved in a certain amount of solvent to obtain a clear solution. Then an anti-solvent was added dropwise into the clear solution and stirred until a solid was precipitated. The results are shown in the table below, and no new crystal form is found by X-ray powder diffraction.

| Solvent | Anti-solvent | Result |
|---|---|---|
| Methanol | Water | Jelly |
| | Isopropyl acetate | Jelly |
| | Methyl isobutyl ketone | Jelly |
| | Toluene | Jelly |
| | Tert-butyl methyl ether | Jelly |

| Solvent | Anti-solvent | Result |
|---|---|---|
| Ethanol | n-heptane | Jelly |
| | Water | Amorphous |
| | Isopropyl acetate | Jelly |
| Tetrahydrofuran | Water | Jelly |
| | n-heptane | Amorphous |
| 2-methyl tetrahydrofuran | Toluene | Jelly |
| | Methyl isobutyl ketone | Jelly |
| dioxane | Water | Jelly |
| | Tert-butyl methyl ether | Jelly |
| Dimethyl sulfoxide | Water | Amorphous |
| | Isopropyl acetate | Jelly |
| Acetone | Water | Jelly |
| | n-heptane | Jelly |
| Dichloromethane | n-heptane | Jelly |
| | Toluene | Jelly |
| Isopropanol | Water | Amorphous |
| Acetonitrile | Water | Amorphous | b. Solvent Volatilization Method

About 10 mg of the compound represented by formula (II) was weighed and added into a 1.5 mL vial, and 0.2-1.0 mL of solvent was added respectively to prepare a clear solution. The undissolved sample was filtered, and then the vial was placed at room temperature and sealed with a parafilm. After piercing 4 small holes, it was allowed to naturally volatilize. The resulting solid was collected and subjected to X-ray powder diffraction test. The results are shown in the following table. The jelly was obtained by the slow volatilization crystallization test.

| Solvent | Result | Solvent (v:v) | Result |
|---|---|---|---|
| Isopropanol | Jelly | Acetonitrile | Jelly |
| Acetone | Jelly | 2-butanone | Jelly |
| Dichloromethane | Jelly | Methanol/Methyl isobutyl ketone 1:1 | Jelly |
| Ethyl acetate | Jelly | Dioxane/Isopropyl acetate 1:1 | Jelly | c. Slow Cooling Method

About 10 mg of the compound represented by formula (II) was weighed and added into a 1.5 mL vial. 0.2-0.6 mL of solvent was added, and the mixture was stirred at 50° C. for 2 hours, and then filtered. The resulting filtrate was cooled from 50° C. to 5° C. at a speed of 0.1° C./min, and maintained at a constant temperature of 5° C. to precipitate a solid. The precipitated solid was collected and subjected to X-ray powder diffraction test. The results are shown in the following table, and no new crystal form is obtained by the slow cooling method.

| Solvent | Result | Solvent (v:v) | Result |
|---|---|---|---|
| Ethyl acetate | Jelly | Anisole | Jelly |
| Acetonitrile | Jelly | Ethanol/Water 1:1 | Jelly |
| 2-butanone | Jelly | 2-methyl tetrahydrofuran/n-heptane 1:1 | Jelly |
| Dichloromethane | Jelly | Acetone/Toluene 1:1 | Jelly | d. Suspending and Stirring Method

About 10 mg of the compound represented by formula (II) was weighed and added into a 1.5 mL glass vial, and 0.2 mL of solvent was added respectively. The resulting suspension was stirred at room temperature and at 50° C. respectively for about 9 days, centrifuged to collect the solid and the X-ray powder diffraction test was performed. The results are shown in the table below, and no new crystal form is obtained in all of the suspending and stirring method.

| Solvent | Stirring temperature | Result | Solvent (v:v) | Stirring temperature | Result |
|---|---|---|---|---|---|
| Isopropanol | 25° C. | Jelly | Toluene | 25° C. | Jelly |
| Acetone | 25° C. | Jelly | Ethanol/n-heptane 1:1 | 25° C. | Jelly |
| Dichloromethane | 25° C. | Jelly | Dimethyl sulfoxide/Water 1:1 | 25° C. | Jelly |
| Ethyl acetate | 25° C. | Jelly | Acetone/Water 984:16 | 25° C. | Jelly |
| Acetonitrile | 25° C. | Jelly | Acetone/Water 95:5 | 25° C. | Jelly |
| 2-butanone | 25° C. | Jelly | Acetone/Water 86:14 | 25° C. | Jelly |
| n-heptane | 25° C. | Amorphous | Acetone/Water 60:40 | 25° C. | Jelly |
| Anisole | 25° C. | Jelly | Methanol/Water 1:1 | 25° C. | Amorphous |
| Methyl isobutyl ketone | 25° C. | Jelly | Acetonitrile/Water 1:1 | 25° C. | Amorphous |
| Isopropyl acetate | 25° C. | Amorphous | Tetrahydrofuran/Water 1:2 | 25° C. | Amorphous |
| Methyl tert-butyl ether | 25° C. | Amorphous | Dimethyl sulfoxide/Water 1:2 | 25° C. | Amorphous |
| Water | 25° C. | Amorphous | Methanol/Water 1:3 | 50° C. | Jelly |
| Water | 50° C. | Jelly | Methanol/Water 1:4 | 50° C. | Jelly |
| Ethyl acetate | 50° C. | Jelly | Acetonitrile/Water 1:3 | 50° C. | Jelly |
| Acetonitrile | 50° C. | Jelly | Tetrahydrofuran/Water 1:4 | 50° C. | Jelly |
| 2-butanone | 50° C. | Jelly | Dimethyl sulfoxide/Water 1:4 | 50° C. | Jelly |
| Anisole | 50° C. | Jelly | 2-methyl tetrahydrofuran/Toluene 1:4 | 50° C. | Jelly |
| Methyl isobutyl ketone | 50° C. | Jelly | Isopropanol/Toluene 1:4 | 50° C. | Jelly |
| Isopropyl acetate | 50° C. | Jelly | Ethanol/n-heptane 1:4 | 50° C. | Jelly |
| n-heptane | 50° C. | Amorphous | Dioxane/n-heptane 1:4 | 50° C. | Jelly |
| Toluene | 50° C. | Jelly | | | | e. Gas-Solid Infiltration Method

About 15 mg of the compound represented by formula (II) was weighed and added into a 3 mL vial. Another 20 mL vial was taken and about 3 mL of solvent was added. The 3 mL vial was opened and placed in the 20 mL vial. The 20 mL vial was sealed and allowed to stand at room temperature for 7 days. The solid was collected and subjected to the X-ray powder diffraction test. The results are shown in the following table, and no new crystal form is obtained by the gas-solid infiltration method.

| Solvent | Result |
| --- | --- |
| Isopropanol | Jelly |
| Acetone | Jelly |
| Dichloromethane | Jelly |
| Ethyl acetate | Jelly |
| Acetonitrile | Jelly |
| 2-butanone | Jelly |
| Chloroform | Jelly |
| Ethanol | Jelly |
| Tetrahydrofuran | Jelly |
| dioxane | Jelly | f. Gas-Liquid Infiltration Method

About 15 mg of the compound represented by formula (II) was weighed and dissolved in a certain amount of solvent, placed into a 3 mL vial. Another 20 mL vial was taken and about 3 mL of anti-solvent was added. The 3 mL vial was opened and placed in the 20 mL vial. The 20 mL vial was sealed and allowed to stand at room temperature. When solid precipitation was observed, the solid was collected and subjected to the X-ray powder diffraction test. The results are shown in the following table, and no new crystal form is obtained by the gas-liquid infiltration method.

| Solvent | Anti-solvent | Result |
| --- | --- | --- |
| Methanol | Water | Amorphous |
| Tetrahydrofuran | Water | Jelly |
| Dimethyl sulfoxide | Water | Jelly |
| Acetone | Water | Jelly |
| Dichloromethane | n-heptane | Jelly |
| dioxane | n-heptane | Jelly |
| Chloroform | n-heptane | Jelly |
| N, N-dimethyl formamide | n-heptane | Jelly |
| Ethanol | n-heptane | Jelly |
| Acetone | Toluene | Jelly |
| Dichloromethane | Toluene | Jelly |
| Isopropanol | Toluene | Jelly |
| 2-methyl tetrahydrofuran | Toluene | Jelly |
| Ethyl acetate | Toluene | Jelly | g. Humidity Induction Method

About 10 mg of the compound represented by formula (II) was weighed and added into a 3 mL vial. The vial was sealed with a parafilm with pierced 4 small holes, placed in a desiccator with a fixed humidity for 9 days. The solid was collected and subjected to the X-ray powder diffraction test. The results are shown in the table below, and no new crystal form is obtained by the humidity induction method.

| Humidity | Result |
| --- | --- |
| 97.30% | Amorphous |
| 75.30% | Amorphous |
| 57.00% | Amorphous |
| 43.20% | Amorphous | h. Temperature Cycling Method

About 15 mg of the compound represented by formula (II) was weighed and added into a 3 mL vial. 0.2-1.0 mL of solvent was added, and the mixture was stirred at 50° C. for 2 hours, and then filtered. The resulting filtrate was subjected to 3 cycles of cooling and reheating. In each cycle, the temperature was reduced from 50° C. to 5° C. at a speed of 0.1° C./min, and then increased to 50° C. in 10 minutes. Then the filtrate was maintained at a constant temperature of 5° C. to precipitate a solid. The precipitated solid was collected and subjected to X-ray powder diffraction test. The results are shown in the following table, and no new crystal form is obtained by the temperature cycling method.

| Solvent | Result | Solvent (v:v) | Result |
| --- | --- | --- | --- |
| Isopropanol | Jelly | Tetrahydrofuran/Water 1:4 | Amorphous |
| Water | Amorphous | Dimethyl sulfoxide/Water 1:4 | Jelly |
| 2-butanone | Jelly | Methanol/Water 1:1 | Amorphous |
| Acetonitrile | Jelly | Acetonitrile/Water 1:1 | Jelly |

The above results indicate that the crystal form of the compound represented by formula (II) cannot be obtained through numerous experiments.

Example 14: Crystallizability Experiment of Other Salt Forms of the Compound of Formula (II)

Hydrochloric acid, sulfuric acid, phosphoric acid, acetic acid, lactic acid, maleic acid, fumaric acid, succinic acid, L-malic acid, adipic acid, L-tartaric acid, hippuric acid, citric acid, mucic acid, ascorbic acid, benzoic acid, gentisic acid, nicotinic acid, ethanedisulfonic acid, oxalic acid, malonic acid, p-toluenesulfonic acid, 2-hydroxyl ethanesulfonic acid and the like were reacted with the compound of formula (II) to prepare the corresponding acid addition salts. The acid addition salts were then screened under the conditions of the above example. However, all of the tested salt forms failed to obtain a crystal form of the compound as characterized by X-ray powder diffraction. The products were mainly jellies, and no crystal was obtained.

The embodiments of the present application have been described above. However, the present application is not limited to the above-mentioned embodiments. Any modification, equivalent replacement, improvement, etc. made within the spirit and principle of the present application shall be included in the protection scope of the present application.

The invention claimed is:

1. An acid addition salt of a compound represented by formula (I) or a prodrug thereof:

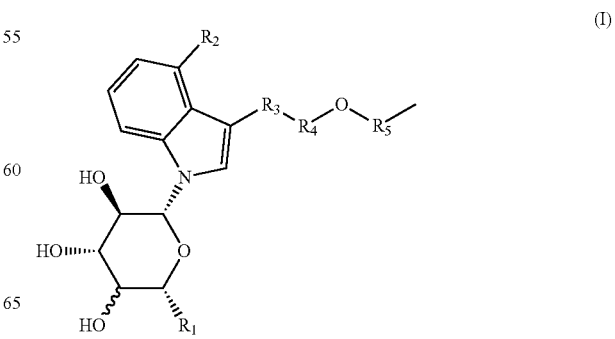

-continued

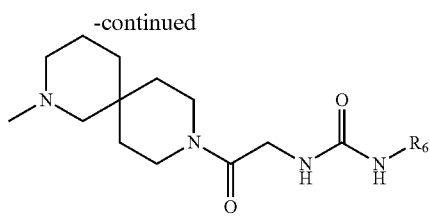

wherein $R_1$, $R_2$ and $R_6$ are the same or different from each other, and independently selected from $C_1$-$C_8$ alkyl which is unsubstituted or optionally substituted with one or more $R_a$;

$R_3$ and $R_5$ are the same or different from each other, and independently selected from —$(CH_2)_n$— which is unsubstituted or optionally substituted with one or more $R_b$;

$R_4$ is selected from $C_6$-$C_{20}$ aryl which is unsubstituted or optionally substituted with one or more $R_c$;

$R_a$, $R_b$ and $R_c$ are the same or different from each other, and independently selected from the group consisting of halogen, hydroxyl, mercapto, nitro and amino;

n is an integer of 1 to 8;

the acid addition salt is D-glucuronate; and the prodrug is an ester formed by a hydroxyl group of the compound represented by formula (I) with a first acid.

2. The acid addition salt according to claim 1, wherein:
$R_1$ is selected from the group consisting of —$CH_3$, —$CH_2CH_3$, —$CH_2Cl$, —$CH_2F$, —$CH_2OH$ and —$CH_2SH$;
$R_2$ is selected from the group consisting of —$CH_3$, —$CH_2CH_3$ and —$CH_2CH_2CH_3$;
$R_3$ is selected from the group consisting of —$CH_2$—, —$(CH_2)_2$— and —$(CH_2)_3$—;
$R_4$ is Ph-;
$R_5$ is selected from the group consisting of —$CH_2$—, —$(CH_2)_2$— and —$(CH_2)_3$—;
$R_6$ is selected from the group consisting of —$CH_3$, —$CH_2CH_3$, —$CH_2CH_2CH_3$, —$CH(CH_3)_2$, —$CH(CH_3)CH_2CH_3$ and —$CH_2CH(CH_3)_2$.

3. A method for preparing the acid addition salt according to claim 1, comprising reacting the compound represented by formula (I) or the prodrug thereof with D-glucuronic acid.

4. The method for preparing the acid addition salt according to claim 3, wherein the reaction is carried out in the presence of a solvent.

5. The method for preparing the acid addition salt according to claim 3, wherein a molar ratio of the compound represented by formula (I) or the prodrug thereof to the acid is greater than or equal to 1:1.

6. The method for preparing the acid addition salt according to claim 3, wherein the reaction is carried out at a temperature in the range of 0-30° C.

7. A crystal form of the acid addition salt or a prodrug thereof according to claim 1.

8. The crystal form according to claim 7, wherein the crystal form is one or more selected from the group consisting of:

(1) a crystal form A of D-glucuronate of the compound represented by formula (II), having one or more characteristic peaks at 4.3±0.2°, 9.2±0.2°, 12.7±0.2°, 13.9±0.2°, 16.9±0.2° and 21.9±0.2° represented by 2θ angle in an X-ray powder diffraction pattern, wherein the compound represented by formula (II) has a structure of:

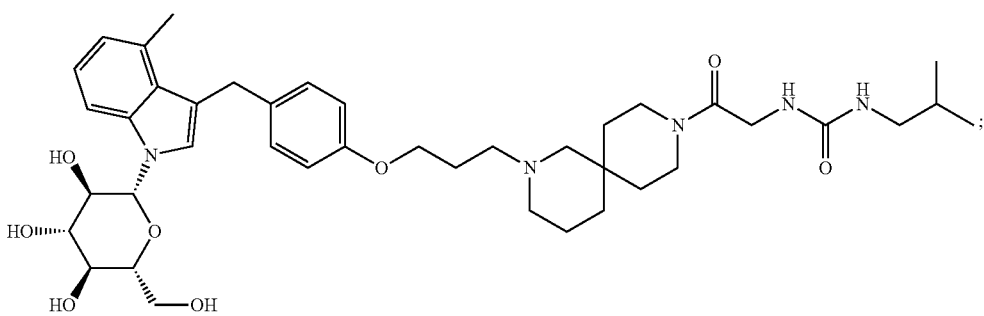

(II)

Figure 5:
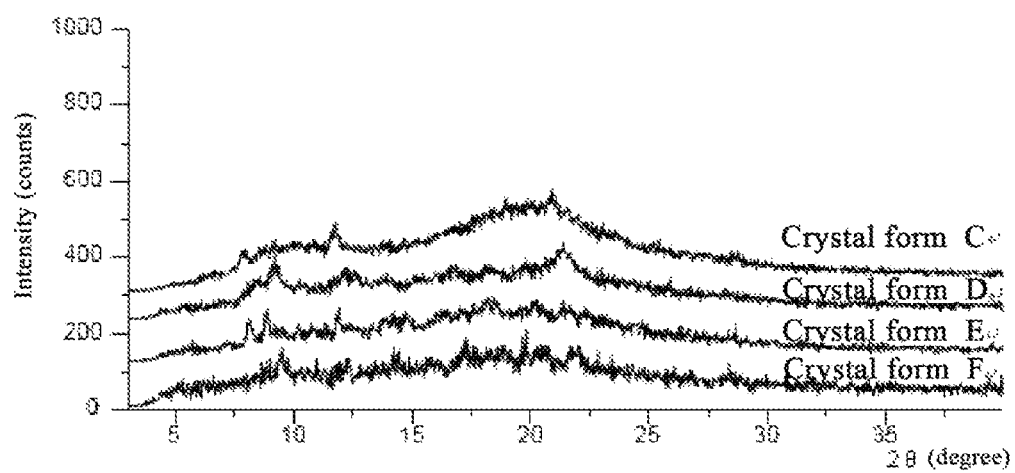
FIG. 5 is an X-ray powder diffraction pattern of the crystal forms C, D, E and F of D-glucuronate of the compound represented by formula (II).

(2) a crystal form D of D-glucuronate of the compound represented by formula (II), having one or more characteristic peaks at 8.5±0.2°, 11.8±0.2°, 18.6±0.2°, and 21.5±0.2° represented by 2θ angle in an X-ray powder diffraction pattern;

(3) a crystal form C of D-glucuronate of the compound represented by formula (II), having an X-ray powder diffraction pattern substantially same as shown in a pattern of a crystal form C in FIG. 5;

(4) a crystal form E of D-glucuronate of the compound represented by formula (II), having an X-ray powder diffraction pattern substantially same as shown in a pattern of a crystal form E in FIG. 5; and (5) a crystal form F of D-glucuronate of the compound represented by formula (II), having an X-ray powder diffraction pattern substantially same as shown in a pattern of a crystal form F in FIG. 5.

9. A method for preparing the crystal form according to claim 8, wherein (1) when the crystal form comprises the crystal form A, the method comprises reacting the compound represented by formula (II) with D-glucuronic acid in a mixed solvent of tetrahydrofuran and water, and drying after completion of the reaction to obtain the crystal form A;

(2) when the crystal form comprises the crystal form D, the method comprises stirring the crystal form A of D-glucuronate of the compound represented by formula (II) in 2-butanone, 1,4-dioxane or a mixture thereof, separating a solid, and drying to obtain the crystal form D;

(3) when the crystal form comprises the crystal form C, the method comprises suspending and stirring the crystal form A of D-glucuronate of the compound represented by the formula (II) in isopropanol, separating a solid, and drying to obtain the crystal form C;

(4) when the crystal form comprises the crystal form E, the method comprises suspending and stirring the crystal form A of D-glucuronate of the compound represented by the formula (II) in toluene, separating a solid, and drying to obtain the crystal form E; and (5) when the crystal form comprises the crystal form F, the method comprises suspending and stirring the crystal form A of D-glucuronate of the compound represented by the formula (II) in dichloromethane, separating a solid, and drying to obtain the crystal form F.

10. A pharmaceutical composition comprising the acid addition salt according to claim 1, and/or the crystal form of the acid addition salt according to claim 1, and a pharmaceutically acceptable excipient.

11. The pharmaceutical composition according to claim 10, wherein the pharmaceutical composition is a formulation that can be administered orally, parenterally, transmucosally, nasally, topically, or sublingually.

12. A method for treating diseases, comprising administering a therapeutically effective amount of the acid addition salt according to claim 1, the crystal form of the acid addition salt according to claim 1, or the pharmaceutical composition comprising the acid addition salt according to claim 1 and/or the crystal form of the acid addition salt according to claim 1 to a patient in need thereof; wherein the diseases include diseases or disorders mediated by SGLT-1 and/or SGLT-2.

13. The acid addition salt according to claim 2, wherein a molar ratio of the compound represented by formula (I) to D-glucuronic acid that forms the acid addition salt is 1:1.

14. The acid addition salt according to claim 2, wherein the compound represented by formula (I) has a structure represented by formula (II):

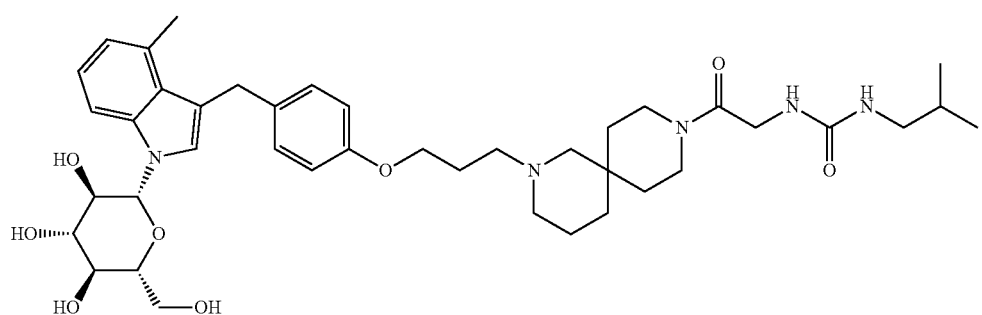

15. The method for preparing the acid addition salt according to claim 4, wherein the solvent is selected from the group consisting of alcohols solvent, ketones solvent, ethers solvent and esters solvent, or any combination thereof.

16. The method for preparing the acid addition salt according to claim 4, wherein the alcohols solvent is selected from the group consisting of methanol, ethanol, isopropanol, butanol, pentanol, decanol, n-dodecyl alcohol, cyclopentanol, cyclohexanol, benzyl alcohol, and phenylethanol, or any combination thereof the ketones solvent is selected from the group consisting of acetone, 2-butanone, methyl isopropyl ketone, methyl cyclohexanone, cyclohexanone, and methyl isobutyl ketone, or any combination thereof; the ethers solvent is selected from the group consisting of diethyl ether, methyl ethyl ether, methyl tert-butyl ether, dipropyl ether, dibutyl ether, 1,4-dioxane, and tetrahydrofuran, or any combination thereof; and the esters solvent is selected from the group consisting of ethyl acetate, hexyl acetate, methyl acetate, and isopropyl acetate, or any combination thereof.

17. The crystal form according to claim 7, wherein the crystal form is a crystal form of D-glucuronate of the compound represented by formula (I) or formula (II) or the prodrug thereof, wherein the compound represented by Formula II has a structure of:

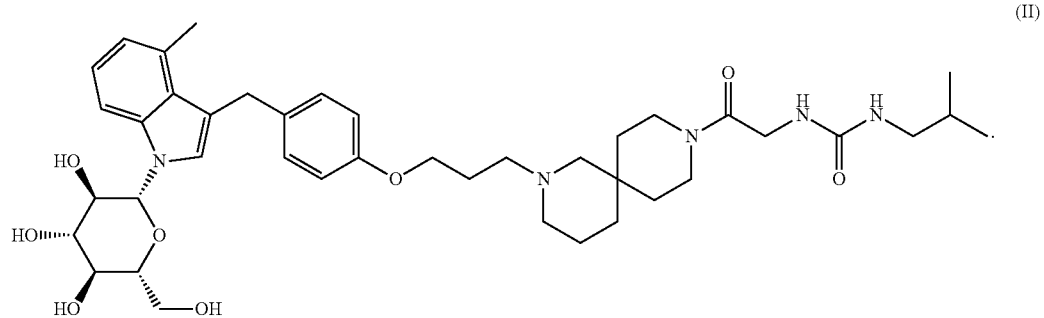 [SMILES: Cc1cccc2c1c(Cc1ccc(OCCCN3CCCC4(CCN(C(=O)CNC(=O)NCC(C)C)CC4)C3)cc1)cn2[C@@H]1O[C@H](CO)[C@@H](O)[C@H](O)[C@H]1O]
(II)
18. The method according to claim 12, wherein the diseases or disorders mediated by SGLT-1 and/or SGLT-2 include hyperglycemia-related disease, impaired glucose tolerance (IGT), impaired fasting glucose (IFG) or metabolic syndrome.
19. The method according to claim 18, wherein the hyperglycemia-related disease is diabetes.
* * * * *